United States Patent

Schoeler et al.

(10) Patent No.: US 9,433,432 B2
(45) Date of Patent: Sep. 6, 2016

(54) SURGICAL CUTTING INSTRUMENT

(71) Applicant: OLYMPUS WINTER & IBE GMBH, Hamburg (DE)

(72) Inventors: Uwe Schoeler, Hoisdorf (DE); Dido Armin Zweibrueck, Hamburg (DE); Andre Scheel, Tespe (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 155 days.

(21) Appl. No.: 14/386,066

(22) PCT Filed: Mar. 20, 2013

(86) PCT No.: PCT/EP2013/000839
§ 371 (c)(1),
(2) Date: Sep. 18, 2014

(87) PCT Pub. No.: WO2013/139473
PCT Pub. Date: Sep. 26, 2013

(65) Prior Publication Data
US 2015/0051628 A1    Feb. 19, 2015

(30) Foreign Application Priority Data
Mar. 21, 2012 (DE) .......... 10 2012 005 536

(51) Int. Cl.
A61B 17/32     (2006.01)
A61B 17/3205  (2006.01)
A61B 17/00     (2006.01)

(52) U.S. Cl.
CPC . *A61B 17/320016* (2013.01); *A61B 17/32002* (2013.01); *A61B 17/3205* (2013.01); *A61B 2017/0088* (2013.01); *A61B 2017/00845* (2013.01)

(58) Field of Classification Search
CPC .......................... A61B 17/32; A61B 17/3205
USPC .......................... 606/170, 171, 172, 174, 108
See application file for complete search history.

(56) References Cited

U.S. PATENT DOCUMENTS 4,603,694 A    8/1986  Wheeler
4,660,267 A *  4/1987  Wheeler .......... A61B 17/32002
                                              29/437

(Continued)

FOREIGN PATENT DOCUMENTS

CN    2368459 Y    3/2000
CN    2576177 Y    10/2003

(Continued)

OTHER PUBLICATIONS

English translation of the International Preliminary Report on Patentability dated Oct. 2, 2014, together with a Written Opinion received in related International Application No. PCT/EP2013/000839.

(Continued)

*Primary Examiner* — Vy Bui
(74) *Attorney, Agent, or Firm* — Scully, Scott, Murphy & Presser, P.C.

(57) ABSTRACT

A surgical milling instrument, comprising two tubular cutters arranged one inside another, each of which has a cylindrical shaft tube, an integrally formed distal end piece in a hollow hemispherical shape, and a cutting window, wherein the outer tubular cutter is non-rotatably mounted on a main body and the inner tubular cutter is mounted in a rotationally driven manner thereon, is characterized in that at least one of the end pieces, in a hole surrounding the axis of the associated shaft tube, has an insert plate connected on the edge thereof to the edge of the hole.

8 Claims, 3 Drawing Sheets

(56) References Cited

Figure 1:
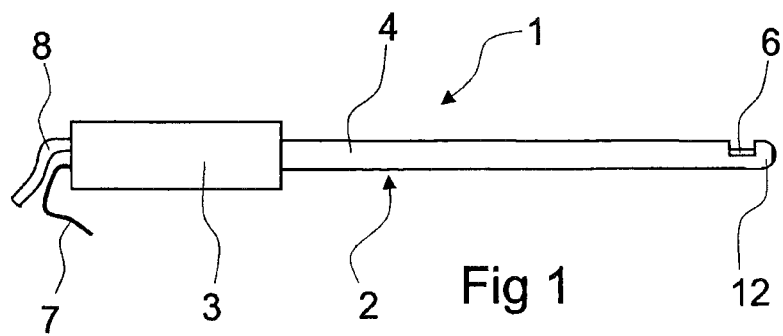

U.S. PATENT DOCUMENTS 5,275,609 A * 1/1994 Pingleton ......... A61B 17/32002
600/566
2009/0048485 A1 2/2009 Heisler

FOREIGN PATENT DOCUMENTS

| CN | 2822524 Y | 10/2006 |
| EP | 0 541 377 A1 | 5/1993 |
| EP | 0 807 413 A1 | 11/1997 |
| WO | 94/26181 A1 | 11/1994 |

OTHER PUBLICATIONS

International Search Report dated Jun. 5, 2013 issued in PCT/EP2013/000839.

* cited by examiner

SURGICAL CUTTING INSTRUMENT

CROSS-REFERENCE TO RELATED APPLICATIONS

The present application is based upon and claims the benefit of priority from PCT/EP2013/000839 filed on Mar. 20, 2013, which claims priority to DE 10 2012 005 536.6 filed on Mar. 21, 2012. The entire contents of each of which is incorporated herein by reference.

The invention relates to a surgical cutting instrument of the type listed in the preamble to claim 1 as well as a tubular cutter of the cutting instrument and a method for producing the tubular cutter.

A generic cutting instrument is known from EP 0 807 413 A1. It serves for removal by cutting of bodily tissues of all types and is used particularly endoscopically, for which purpose it is suitable due to an elongated shaft tube.

The tubular cutters are mounted on a main body, namely the outer tubular cutter is non-rotatably mounted and the inner tubular cutter is mounted rotationally-driven. An electromotor is provided e.g. in the main body. The length of the shaft tube is adjusted to the surgical conditions, e.g. for working in a joint or in the abdominal cavity. The inner tubular cutter rotates at a high rotational speed. By this means, the cutting windows are moved relative to each other in the shaft tubes. entering into the cutting windows is cut away by the shear movement of the edges of the cutting window to each other.

For this purpose, the tubular cutters must glide as closely as possible on each other and require a good mounting on each other for long-term safe operation at high rotational speeds. Bearings between the cylindrical shaft tubes are thereby provided. In the region of the hemispherically-shaped end pieces, an axial mounting of the shaft tubes on each other is necessary.

According to the prior art, the hemispherically-shaped end pieces lie completely on each other for axial mounting. This indeed results in a good axial mounting, but also in a radial mounting in the spherical region.

An additional radial mounting in the distal end piece of the tubular cutter is, however, unfavorable, since this mounting, together with the mountings in the region of the cylindrical shaft tube, results in a redundancy, which leads to wear and jamming hazards.

A further disadvantage of the known design is the very expensive production of the distal end pieces formed in a hollow hemispherical shape, which must be formed in a highly exacting fit.

In the known manufacturing process, the shaft tube is drawn into the spherical shape by pressing on the distal end and by this means closed, up to a small hole, which must be closed by the very expensive deposition of material.

It is the object of the present invention to cost-efficiently improve the problems of the axial mounting in a generic cutting instrument.

This problem is solved by the features of the characterizing part of claim 1 and by claims 7 and 8.

According to the invention, an insert plate is inserted in an end piece which surrounds the axis of the shaft tube. By this means, the closing of the hole remaining from indenting the tube is unnecessary. Since the plate is inserted, it can be processed separately from the tube and can be formed very easily in a suitable way for the axial mounting. This work on the plate can be carried out substantially more easily, if said plate is still separate from the tubular cutter.

The end pieces, with their insert plates, can be formed exactly hemispherically, wherein a radial mounting would also result, in addition to the axial mounting, in the region of the end pieces, which radial mounting, however, is undesired. Therefore, care should therefore be taken, that there are only axial contacts, and no radial contacts, in the region of the hemispherically-shaped distal end pieces. The features of claim 2 are advantageously provided for this purpose. If an insert plate protrudes with the center of the surface thereof lying towards the other end piece over the sphere surface, then this results in the axial contact between the two end pieces in the region of this protruding center, by which means a very clean, axial mounting point results, namely without radial guidance. This form of the insert plate can thereby be provided on the outer tubular cutter as well as on the inner tubular cutter. The plate must thereby protrude inward on the outer tubular cutter, and it must be formed protruding outward on the inner tubular cutter.

The inner surface of the insert plate is thereby formed advantageously flat according to claim 3. If this insert plate is provided on the outer tubular cutter, then the flat inner edge provides a good contact for the protruding region of the insert plate on the inner tubular cutter, wherein every radial guide is foregone in this region.

The outer surface of the insert plate is thereby advantageously formed according to claim 4 as part of the sphere surface. A completely undistorted spherical surface thus results on the outer side of the tubular cutter, by which means e.g. injuries are prevented.

Advantageously according to claim 5, in this form of the insert plates with flat inner surface and spherical outer surface, the two insert plates can be formed identically, which simplifies warehousing and costs.

The insert plate can have largely any peripheral shape, e.g. square. The hole in the end piece, which should receive the insert plate, must then be correspondingly produced. Preferably, according to claim 6, this hole is formed as a drilled hole arranged concentric to the axis of the associated shaft tube, by which means the production of the hole in rotating processing is simplified very much. The end plate suitable thereto can also be produced in a cost-efficient way using cylindrical lateral faces.

Claim 7 protects the tubular cutter of the cutting instrument.

The inventive tubular cutter can be produced in various ways, preferably according to claim 8. Initially thereby, preferably in a rotating operation method, one end of the shaft tube is pressed into the hemispherical shape until a small opening remains there, which opening is smaller than the hole in which the insert plate should be inserted. The hole for the insert plate is subsequently introduced, e.g. using a drill, in order to then insert the insert plate into this hole and subsequently to connect said insert plate to the shaft tube on the edge, for example by soldering, welding, or the like.

Figure 2:
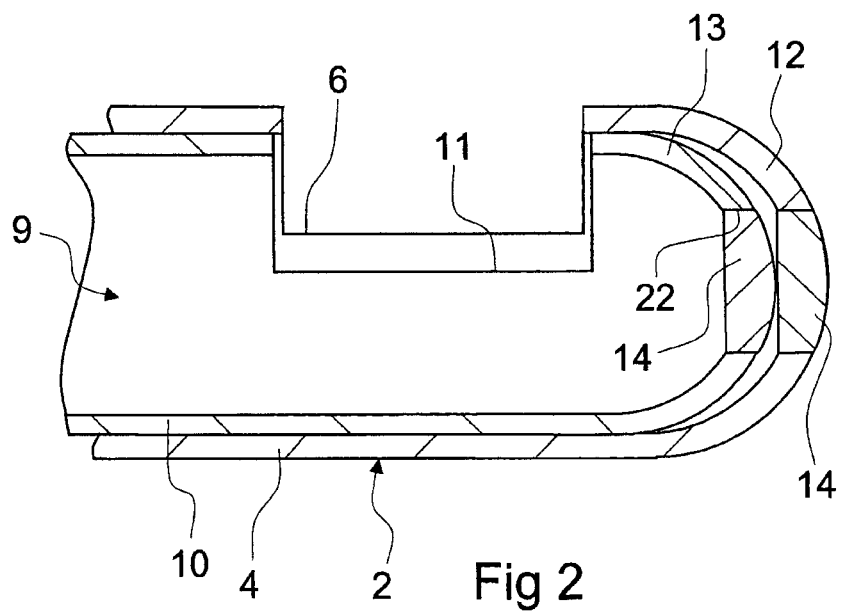
Figure 3:
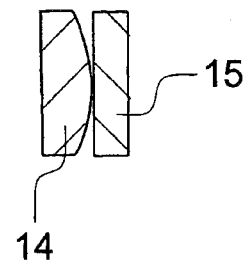
Figure 4:
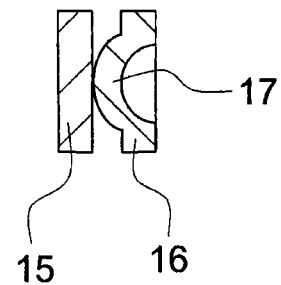
Figure 5:
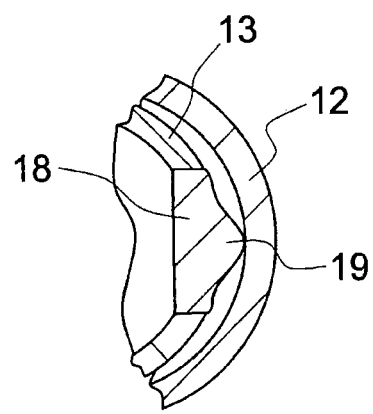
Figure 6:
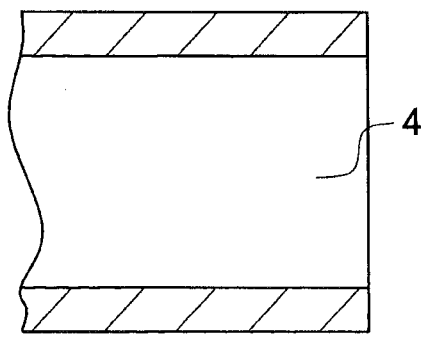
Figure 7:
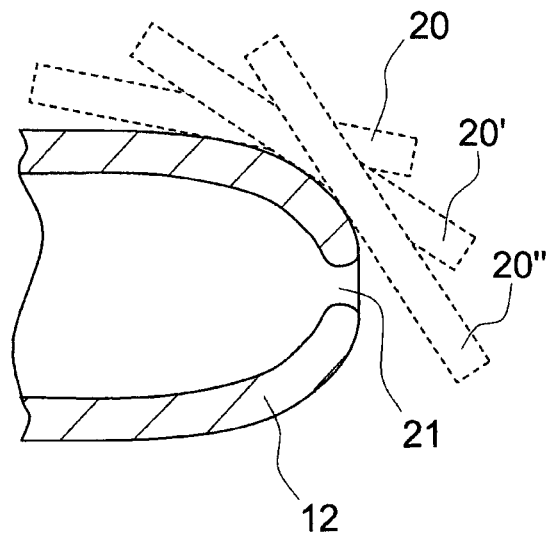
Figure 8:
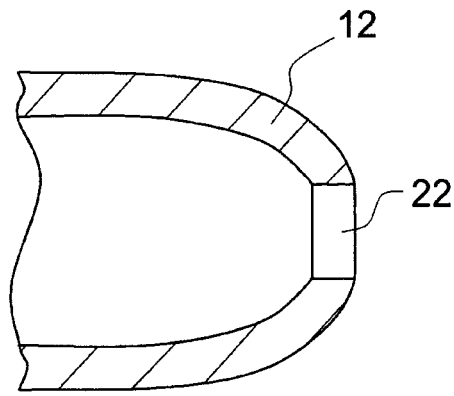

The invention is depicted in an exemplary and schematic way in the drawings. As seen in:

FIG. 1 a side view of an inventive cutting instrument,

FIG. 2 an axial view through the enlarged distal end region of the cutting instrument of FIG. 1 with the depiction of the region of the axial support by means of two insert plates, FIGS. 3 & 4 a depiction of the insert plates in other embodiments, FIG. 5 a depiction of the region of the axial contact with only one insert plate, and FIGS. 6-8 three production steps to form the distal end piece in an axial view through the distal end region of a tubular cutter.

FIG. 1 shows an inventive cutting instrument 1 comprising an outer tubular cutter 2 which is mounted on a main body 3. The main body 3 can be used as a handgrip and is formed accordingly. The outer tubular cutter 2 has an elongated, cylindrical shaft tube 4 and a hemispherically shaped distal end piece 12. A cutting window 6 is formed in the tubular cutter 2 close to the distal end piece 12.

An electromotor (not visible in FIG. 1) is arranged in the main body 3, which electromotor is supplied via a cable 7 externally outbound from the main body 3. In addition, a hose 8 exits from the main body 3, which hose is connected e.g. to a suitable suction device in order to suction out the interior of the shaft tube 4.

FIG. 2 shows in an enlarged view the distal end region of the outer tubular cutter 2. It can be seen that an inner tubular cutter 9 with the cylindrical shaft tube 10 thereof is arranged in said region in a good axial mounting in the cylindrical shaft tube 4 of the outer tubular cutter 2. At the point of the cutting window 6 in the outer tubular cutter 2, the inner tubular cutter 9 also has a matching cutting window 11.

The inner tubular cutter 9 is driven by the motor in the main body 3 and rotates around the common axis of the two tubular cutters 2 and 9. The cutting windows 6 and 11 thereby move relative to each other such that the edges thereof cut away penetrating tissue. At higher rotational speeds, there results a very good cutting effect. Material that is cut away arrives through the cutting windows 6, 11 into the interior of the inner tubular cutter 9 and is suctioned out from there via the suction tube 8.

FIG. 2 shows that the distal end piece 12 of the outer tubular cutter 2 is formed likewise in a hollow hemispherical shape like the distal end piece 13 of the inner tubular cutter 9. If the distal end pieces 12 and 13 were thus arranged, as this is described in EP 0 807 413 A1, then the inner surface of the outer end piece 12 would correspond exactly to the outer surface of the inner end piece 13 and align flat with the same.

With this type of spherical surface contact between the two end pieces 12 and 13, there would result an axial support, which is necessary and desired; however, also a radial support between the tubular cutters 2 and 9 results, which is undesired here at the distal end pieces, since a redundancy would result together with the other mountings of the tubular cutters in the region of the cylindrical shaft tube 4 and 10.

The inventive design according to FIG. 2 ensures that a support of the tubular cutters 2 and 9 on each other results only exactly at a point which lies in the axis of the tubular cutters. The other regions of the hemispherical surface are held separated, such that no axial supporting contact of the spherical surface results in the end pieces 12 and 13.

This is achieved in the embodiment of FIG. 2 in that the inner side of the outer end piece 12 is formed flat in a center region. This region thus protrudes axially over the inner spherical surface of the end piece 12 and ensures that clearance is maintained between the end pieces 12 and 13, even if, as depicted, the outer surface of the inner end piece 13 maintains an exact spherical shape.

As FIG. 2 shows, in this center region, both end pieces 12 and 13 can be formed identically.

As FIG. 2 also shows, the center regions of the end pieces 12 and 13 are formed as identical insert plates 14. By this means, the production of the center regions of the end pieces 12 and 13, which require a precise fit, is vastly simplified.

The insert plates 14 can, e.g., be produced in a manner very different from the remaining parts of the tubular cutter.

FIG. 3 shows, in a design otherwise concurring with the depiction of FIG. 2, which design is omitted for graphic simplification, only the two insert plates; however, in a different design in this case. The insert plate 14 of the inner tubular cutter 9 corresponds with the design of FIG. 2. The insert plate 15 in the outer tubular cutter 2 is flat on the inner surface thereof, as is also the case for the insert plate 14; however, in this embodiment it is also flat on the outer surface, which is depicted here as an example of a possible embodiment.

FIG. 4 shows a further variant of the insert plates, wherein the insert plate on the inner tubular cutter is the plate 15, which is flat on both surfaces, and the outer insert plate 16 is of a completely different shape. It protrudes inwardly with a bulge 17.

Yet a further variant of the axial mounting is depicted in FIG. 5. In this case, the outer end piece 12 is formed without an insert plate. In the inner end piece 13, an insert plate 18 is arranged, which has a clear protrusion 19 in the distal direction. In this embodiment, the outer end piece 12 can also be formed with an insert plate, for reasons of simplifying the production, which insert plate would have a spherical shape on both sides.

All embodiments of the axial support, which are depicted in FIGS. 2 to 5, result in the same effect, namely a point shaped contact of the end pieces 12 and 13 exactly at the rotational axis of the inner tubular cutter 9, wherein the remaining parts of the hemisphere remain without contact between the end pieces 12 and 13.

FIGS. 6 and 8 serve to explain an advantageous method for producing the tubular cutter 2, which can also be used for producing the tubular cutter 9, which can be formed identically except for the diameter, as FIG. 2 shows.

This thereby proceeds from a straight piece of tube, the distal end region thereof is shown in FIG. 6. The example depicted is the end region of a cylindrical shaft tube 4. The shaft tube 4 is cut off from an endless tube e.g. using the straight cutting surface depicted.

The piece of tube 4 is rotatably driven e.g. on a lathe and the depicted end region is rotatably reformed using a spinning tool, such that that the depicted end is indented to be increasingly smaller in diameter until the rounded form of the end piece 12 results as depicted in FIG. 7. For the indenting, e.g. a straight tool 20 depicted in FIG. 7 can be used, which is gradually angled increasingly across the points 20, 20', 20", in order to indent the tube 4 out of the straight shape according to FIG. 6 into the rounded form according to FIG. 7.

During this production, an opening 21 remains, which can be closed by welding or a similar material application technology. Preferably, however, as is depicted in FIG. 8, a drilled hole 22 is introduced in the axis of the tube 4, which drilled hole matches, in the diameter thereof, the outer diameter of the insert plates, e.g. the insert plate 14 according to FIG. 2. An insert plate 14 can then be inserted therein, as this is depicted in FIG. 2, and fixed on the edge e.g. by welding.

The insert plates 14, 15, 16, or 18 are exposed to increased wear at the point of contact thereof, and therefore consist advantageously of a particularly wear-resistant material, like carbide or ceramic.

The invention claimed is:

1. A surgical cutting instrument comprising two tubular cutters arranged one inside another, each of which having a cylindrical shaft tube, a distal end piece in a hollow hemispherical shape integrally formed with the cylindrical shaft tube and a cutting window, wherein the outer tubular cutter is non-rotatably mounted on a main body and the inner tubular cutter is mounted in a rotationally driven way thereon, wherein at least one of the end pieces has, in a hole surrounding the axis of the associated shaft tube, an insert plate connected on the edge thereof to the edge of the hole.

2. The surgical cutting instrument according to claim 1, wherein the insert plate is formed projecting with the center surface thereof lying towards the other end piece over the sphere surface.

3. The surgical cutting instrument according to claim 2, wherein the inner surface of the insert plate is formed as flat.

4. The surgical cutting instrument according to claim 3, wherein the outer surface of the insert plate is formed as part of the spherical surface.

5. The surgical cutting instrument according to claim 3, wherein the insert plates of both tubular cutters are formed identically.

6. The surgical cutting instrument according to claim 1, wherein the hole is formed as a drilled hole arranged concentric to the axis of the associated shaft tube.

7. A tubular cutter of a cutting instrument according to claim 1, having a cylindrical shaft tube, a distal end piece in a hollow hemispherical shape integrally formed with the cylindrical shaft tube, wherein the end piece has, in a hole surrounding the axis of the associated shaft tube, an insert plate connected on the edge thereof to the edge of the hole.

8. A method for producing a tubular cutter according to claim 7, wherein one end of the shaft tube is indented to a hemispherical shape until an opening remains, which opening is smaller than the area of the hole, the hole is then introduced and the insert plate is inserted in said hole and is subsequently fixed at the edge.

* * * * *